United States Patent [19]

Gehrz et al.

[11] Patent Number: 5,124,440
[45] Date of Patent: Jun. 23, 1992

[54] ANTIBODY AND T CELL RECOGNITION SITES ON GLYCOPROTEINS COMPRISING THE GCI COMPLEX OF HUMAN CYTOMEGALOVIRUS

[75] Inventors: Richard C. Gehrz, Mendota Heights, Minn.; Mark F. Stinski, North Liberty, Iowa; Bruce I. Kari, Minneapolis, Minn.; Yung-Nan Liu, Roseville, Minn.

[73] Assignees: The Childrens Hospital, Inc., St. Paul, Minn.; University of Iowa Research Foundation, Iowa City, Iowa

[21] Appl. No.: 328,231

[22] Filed: Mar. 24, 1989

Related U.S. Application Data

[63] Continuation-in-part of Ser. No. 83,502, Aug. 7, 1987, which is a continuation-in-part of Ser. No. 933,789, Nov. 24, 1986, abandoned, which is a continuation-in-part of Ser. No. 214,302, Jul. 1, 1988, abandoned.

[51] Int. Cl.$^5$ ................. C07K 15/04; A61K 39/12
[52] U.S. Cl. ................. 530/395; 530/826; 424/89
[58] Field of Search ............. 530/395, 826; 424/89

[56] References Cited

FOREIGN PATENT DOCUMENTS 0122841 3/1984 European Pat. Off.
0236145 9/1987 European Pat. Off.

OTHER PUBLICATIONS

*Journal of General Virology*, vol. 69, 1988, SGM (GB), D. R. Gretch et al.: "Characterization of a Human Cytomegalovirus Glycoprotein Complex (gCI)", pp. 1205–1215.

*Virology*, vol. 167, 1988, Academic Press, Inc., R. R. Spaete et al.: "Human Cytomegalovirus Strain Towne Glycoprotein B Is Processed by Proteolytic Cleavage", pp. 207–225.

*The EMBO Journal*, vol. 5, No. 11, 1986, IRL Press Limited, (Oxford, GB), M. P. Cranage et al.: "Identification of the Human Cytomegalovirus Glyprotein B. Gene and Induction of Neutralizing Antibodies via its Expression in Recombinant Vaccinia Virus", pp. 3057–3063.

*Journal Exp. Medicine*, vol. 168, Sep. 1988, The Rockefeller University Press, L. K. Borysiewicz et al.: "Human Cytomegalovirus-Specific Cytotoxic T. Cells", pp. 919–931.

*Primary Examiner*—David L. Lacey
*Assistant Examiner*—Shelly J. Guest
*Attorney, Agent, or Firm*—Merchant, Gould, Smith, Edell, Welter & Schmidt

[57] ABSTRACT

Glycopeptides of the gcI (gB) complex of human cytomegalovirus are disclosed. They possess unique B cell and T cell epitopes not present in other gcI glycopeptides. Glycopeptide fragments which comprise minimal antigenic determinants of the gcI complex are also disclosed, as are recombinant expression vectors, vaccines, and diagnostic methods.

8 Claims, 14 Drawing Sheets

LOCALIZATION OF B CELL EPITOPES ON HCMV-gB POLYPEPTIDE

```
                                                        470                                         480
Ser Thr Asp Gly Asn Asn Ala Thr His Leu Ser Asn Met Glu Ser Val His Asn Leu Val Tyr Ala Gln
                            490                                         500
Leu Gln Phe Thr Tyr Asp Thr Leu Arg Gly Tyr Ile Asn Arg Ala Leu Ala Gln Ile Ala Glu Ala Trp
                            510                                         520
Cys Val Asp Gln Arg Arg Thr Leu Glu Val Phe Lys Glu Leu Ser Lys Ile Asn Pro Ser Ala Ile Leu
530                                         540                                         550
Ser Ala Ile Tyr Asn Lys Pro Ile Ala Ala Arg Phe Met Gly Asp Val Leu Gly Leu Ala Ser |Cys| Val
                            560           18F9              570
Thr Ile Asn Gln Thr Ser Val |Lys Val Leu Arg Asp Met| Asn Val Lys |Glu Ser| |Pro| Gly Arg |Cys| Tyr
580                                         590           41C2*
Ser |Arg| Pro Val Val Ile Phe Asn Phe Ala Asn Ser Ser Tyr |Val Gln Tyr Gly Gln Leu| Gly Glu Asp
600                                         610                                         620
Asn Glu Ile Leu Leu Gly Asn His Arg Thr Glu Glu |Cys| Gln Leu Pro Ser Leu Lys Ile Phe Ile Ala
                            630                                         640
Gly Asn Ser Ala Tyr Glu Tyr Val Asp |Tyr| Leu Phe Lys Arg Met Ile Asp Leu Ser Ser Ile Ser Thr
                            650                                         660
Val Asp Ser Met Ile Ala Leu Asp Ile Asp Pro Leu Glu Asn Thr Asp Phe Arg Val Leu Glu Leu Tyr
```

TOWNE HCMV-gB SEQUENCE (SPAETE ET AL, VIROLOGY 167:207, 1988)

* TENTATIVE ASSIGNMENT

FIG. 1A

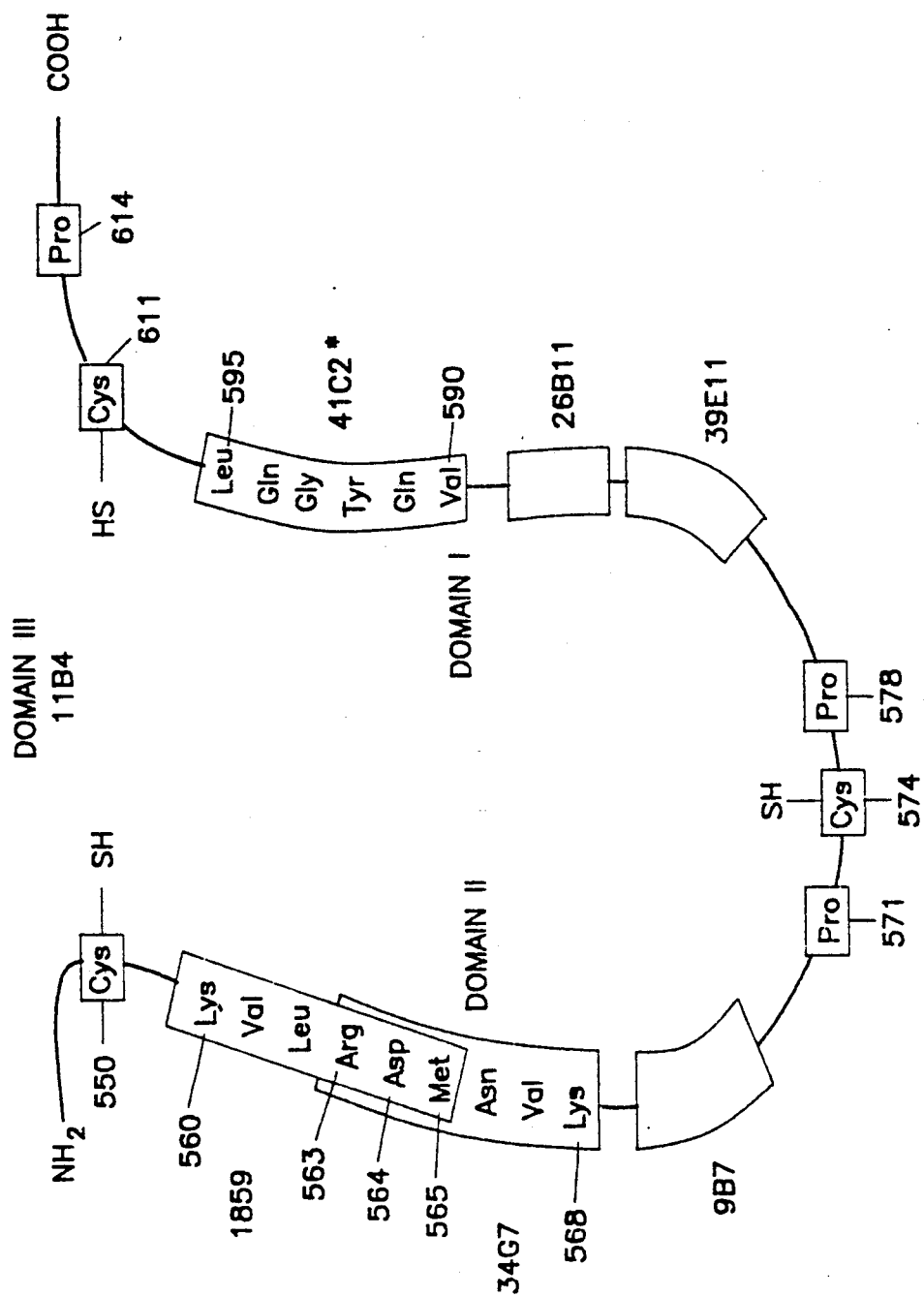
FIG. 1B  HYPOTHETICAL MODEL OF TOPOGRAPHICAL ANTIGENIC MAP FOR HCMV GLYCOPROTEIN(S) IN gcI COMPLEXES

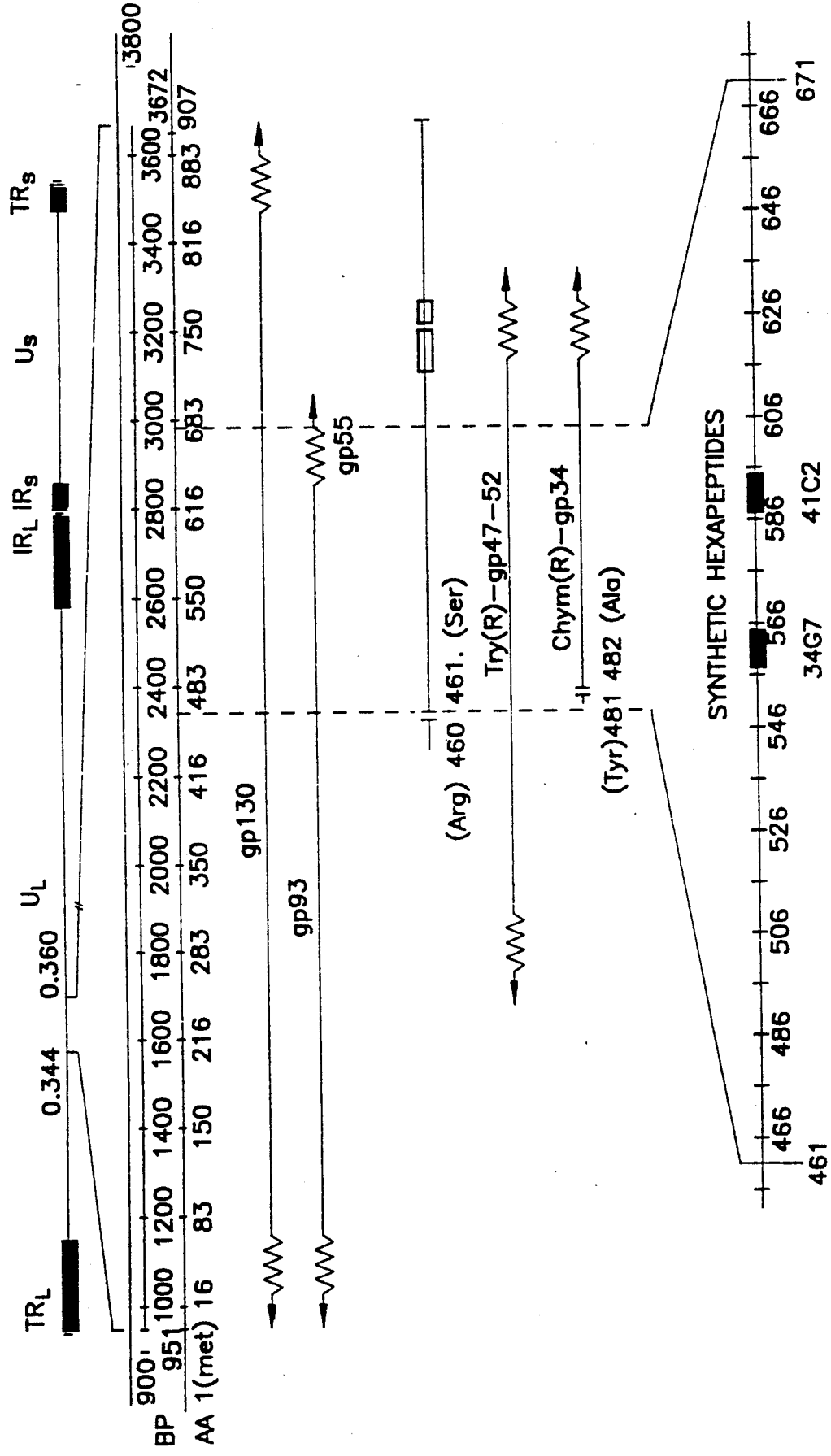
FIG. 2 MOLECULAR ANALYSIS OF ANTIGENIC DOMAINS OF HCMV-gB

FIG. 3 PLASMID MAP FOR SP 6 CLONING VECTOR pSP65
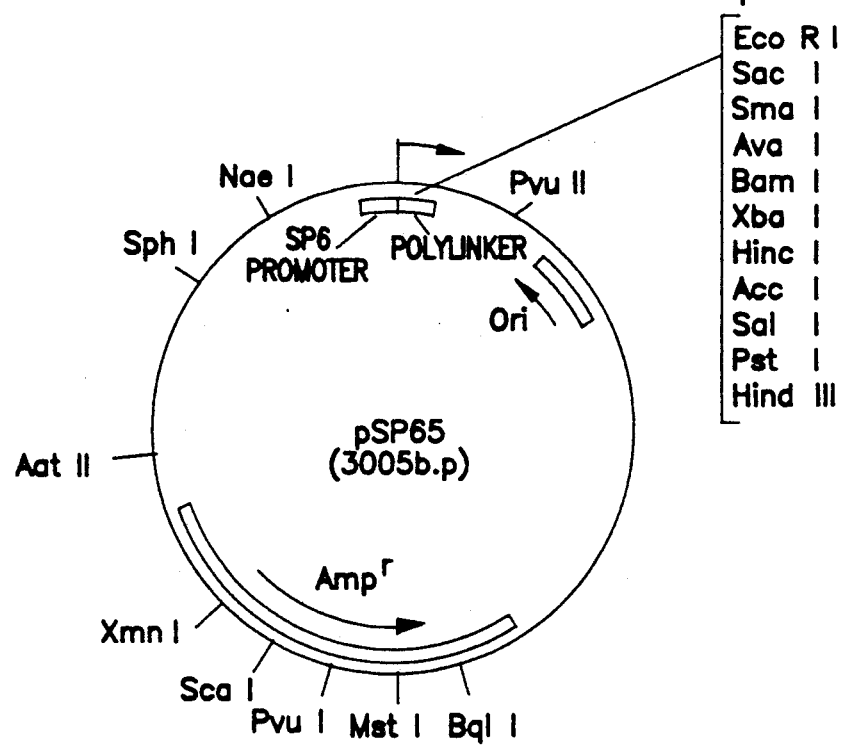
FIG. 4
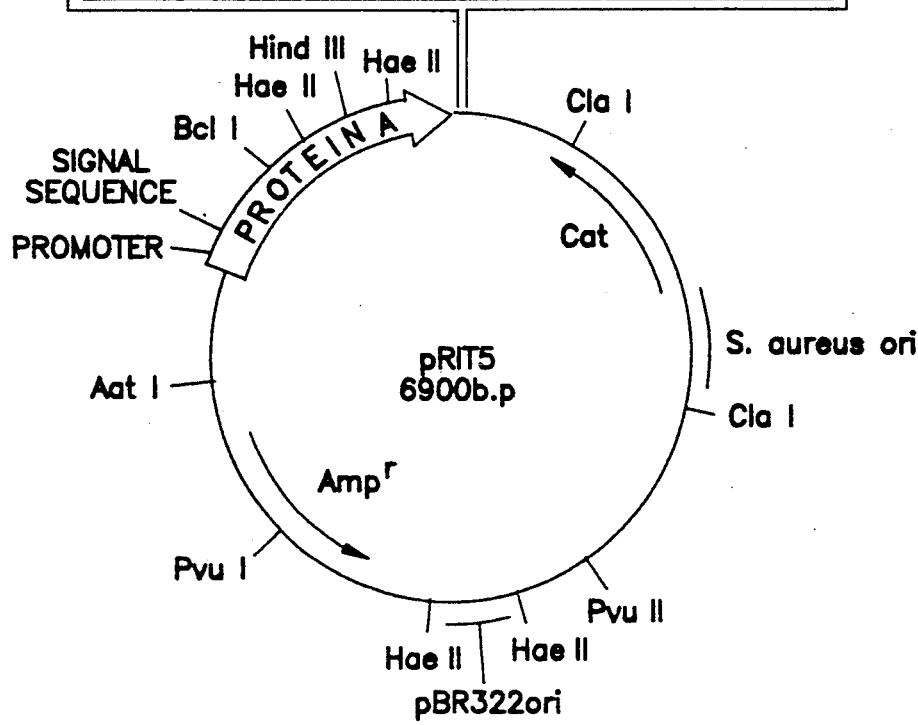

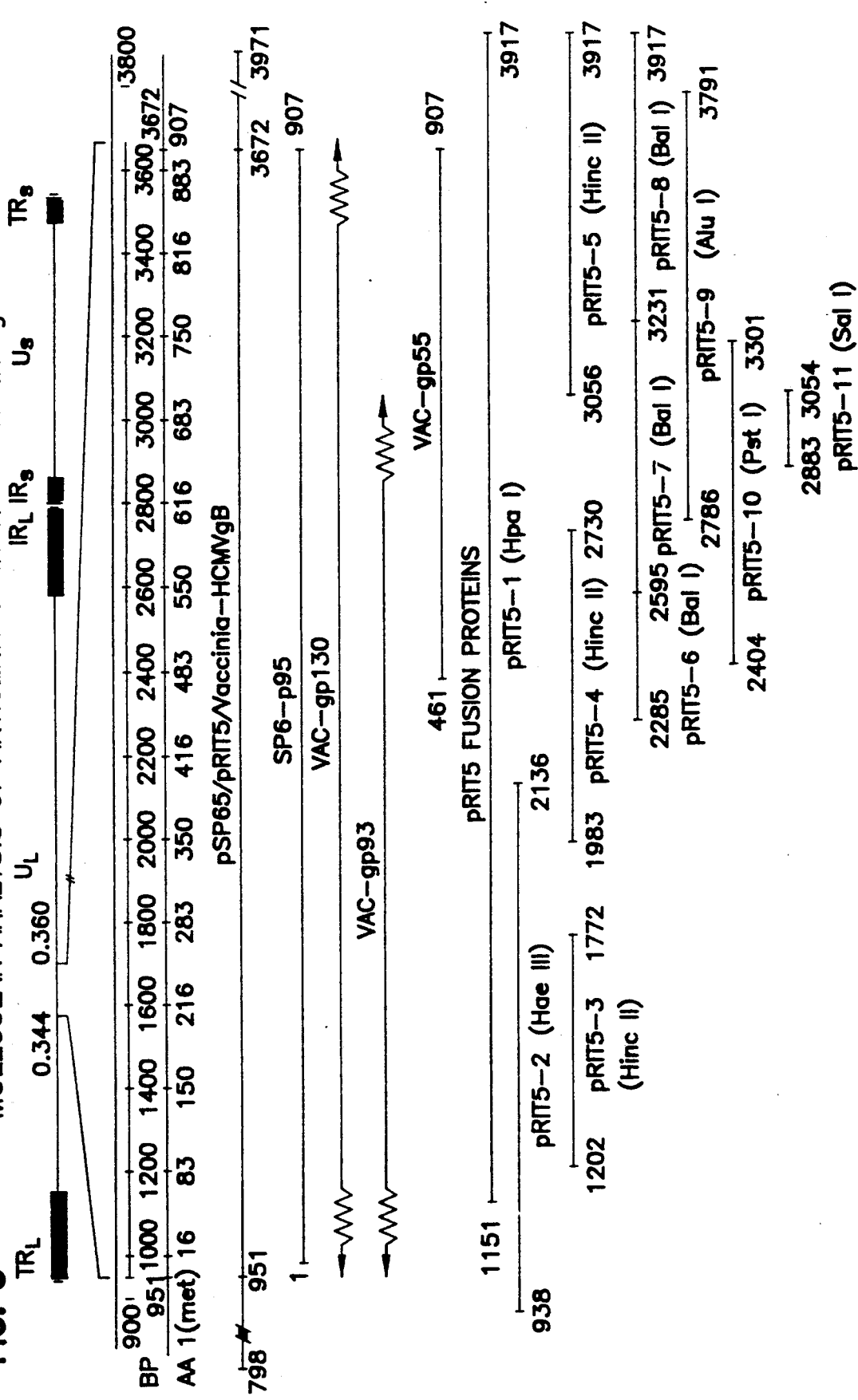
FIG. 5  MOLECULAR ANALYSIS OF ANTIGENIC DOMAINS OF HCMV-gB

PLASMID MAP FOR VACCINIA TK
TRANSFER VECTOR pSC11 AND pSC11t

|  | TOWNE |
|  | AD169 |

```
-949  CTG.AGAAGGTTTCGGAGGTGGGCTATGCCAAGGTGATCGTTGCATCAAAACGCAGGAGCGTCTGACTAGCAAACTCATCGATGTCAACCTAGTGTGGGCCCTTGTCTGTCTGGACTTTAT
      CTGCAGAAGGTCTCGGAGGTGGGCTATGCCAAGGTGATCGTTGCATCAAAACGCAGGAGCGTCTGACTAGCAAGCTCATCGATGTCAAGCTAGTGTGGGCCCTTGTCTGTCTGGACTTTAT

-830  CTCTAAGCTCATGAATGGGTTTCTATACCGCAGCCAATACCACCAGGACCAAGACTGTGGTGGACGTGGGGATCAGTTCACGTACGATGAGCACCTGTATGTGGTCAATAACCTGATCC
      CTCTAAGCTCATGAATGGGTTTCGTCTACCGCAGCCAATACCACCAGGACCAAGACTGGTGGACGTGGTGATCAGTTCACCTACGATGAGCACCTGTATGTGGTCAATAACCTGATCC

-711  ACAAGAGTCTGCCTGTGCAATCCCTCCCGCTACTGGGTCAGCAGATCTACGAGTTGTGTAACGGCCCCTCTTCCACACACTGCACCGATCGCTATCCCCTCTCTCACAATGTGGACATG
      ACAAGAGTCTGCCTGTGCAATCCCTCCCGCTACTGGGTCAGCAGATCTACGAGTTGTGTAACGGCCCCTCTTCCACACACTGCACCGATCGCTATCCCCTCTCTCACAATGTGGACATG

-592  GCCTATGCCTGCGACAACGCGGGCGTACTACCCCACGTCAAGGACGATTTGGTCAAATGCGCGGAAGGTACCGTGTATCCCAGTGAGTGGTGATGGTGTGAAGTACATGGGTTTTTCAA
      GCCTATGCCTGCGACAACGCGGGCGTACTACCCCACGTCAAGGACGATTTGGTCAAATGCGCGGAAGGTACCGTGTATCCCAGTGAGTGGTGATGGTGTGAAGTACATGGGTTTTTCAA

-473  TTTTTCGGACTGTCAGGATCTAAACGTGCTGCAGAAGGAGAGATGTGATGCACGTGCCGGGGAGCTCGTCTCCGTCGCCGCTATATAATGAAACTTTCGGGAAACAACTCTCGATCGGT
      TTTTTCGGACTGTCAGGACCTAAACGTGCTGCAGAAGGAGAGATGTGATGCACGTGCCGGGGAGCTCGTCTCCGTCGCCGCTATATAATGAAACTTTCGGGAAACAACTCTCGATCGGT

-354  GCCTGCCGACGAACTGCACCCGACGAGAGATGTGATTCTCACGTACGTCATCCTGCTTCGTCGCTGCTATAACAAAGAGTGGCCGCTGGCCGCTGGCCCGCTCCAAGATCTTTATAAGTCCAAAGATCTTTATAAGTCCAAAGATCTATCTCCTCTC
      GCCTGCCGACGAACTGCACCCGACGAGAGATGTGATTCTCACGTACGTCATCCTGCTTCGTCGCTGCTATAACAAAGAGTGGCCGCTGGCCGCTGGCCCGCTCCAAGATCTTTATAAGTCCAAAGATCTTTATAAGTCCAAAGATCTATCTCCTCTC

-235  TACAGGCATCTGTCCAGACCGGATGAGAGTGGCGACGTGCCAACAGCTCCCACCCTGACGGCCCGCGCGCCGGGGTGCCTTCAGGGAGCCGGACCGACC
      TACAGGCATCTGTCCAGACCGGATGAGAGTGGCGACGTGCCAACAGCTCCCACCCTGACGGCCCGCGCGCCGGGGTGCCTTCAGGGAGCCGGACCGACC

-116  TTGGCTGCCAAGTCCGTACCCTCCTCCTCGACCCGGGGTGCGGGTGTTTCCCGGAGGGTCCCGGAGGGTGTTTCCCGGAGGGTGTTGCCCGGATTTGGCCCCGGACGAAC
      TTGGCTGCCAAGTCCGTATCCGTATCCCTCCTCGACTCGCGGGTGCGGGTGTTTCCCGGAGGGTCCCGGAGGGTGTTTCCCGGAGGGTGTTGCCCGGATTTGGCCCCGGACGAAC
```

```
                                                                                                    748
           Leu Gly Ala Ala Gly Lys Ala Val Gly Ile Gly Ala Val Gly Val Val Glu Gly Val Ala Thr Phe Leu
           CTG GGC GCC GCG GGA AAG GCC GTT GGC GTA GCC ATT GGG GCC GTC GTG GAA GGC GTT GCC ACC TTC CTC
           CTG GGC GCC GCG GGA AAG GCC GTT GGC GTA GCC ATT GGG GCC GTC GTG GAA GGC GTT GCC ACC TTC CTC
           Leu Gly Ala Ala Gly Lys Ala Val Gly Ile Gly Ala Val Gly Val Val Glu Gly Val Ala Thr Phe Leu
      2155                                                      758                                778
           Lys Asn Pro Phe Gly Ala Asn Thr Ile Ile Ile Ala Val Leu Val Tyr Leu Ile Tyr Thr Arg Gln Arg Arg Leu
           AAA AAC CCC TTC GGA GCC TTC ACC ATC ATC ATC GCC GTC CTC GTG TAT CTC TTG ATC TAT ACT CGA CAG CGG CGT CTC
           AAA AAC CCC TTC GGA GCC TTC ACC ATC ATC ATC GCC GTA GTC CTG TAT CTC TTG ATC TAT ACT CGA CAG CGG CGT CTC
           Lys Asn Pro Phe Gly Ala Asn Thr Ile Ile Ile Ala Val Val Val Leu Tyr Leu Leu Ile Tyr Thr Arg Gln Arg Arg Leu
      2245                                                      768                                      808
           Cys Met Gln Pro Leu Gln Asn Leu Phe Pro Tyr Leu Val Ser Ala Asp Gly Thr Thr Val Ile Tyr Asn Thr Gly Lys Asp Thr Ser Leu
           TGC ATG CAG CCG CTG CAG AAC CTC TTT CCC TAT CTC GTG TCC GAC GGG ACC ACC GTG ATT TCG GGC AAC ACC AAA GAC ACG TCG TTA
           TGC ACG CCG CTG CAG AAC CTC TTT CCC TAT CTG GTG TCC GAC GGG ACC ACC GTG ATT TCG GGC AGC ACC AAA GAC ACG TCG TTA
           Cys Thr Gln Pro Leu Gln Asn Leu Phe Pro Tyr Leu Val Ser Ala Asp Gly Thr Thr Val Ile Tyr Ser Thr Lys Asp Thr Ser Leu
      2335                                                      798                                838
           Gln Ala Pro Pro Ser Tyr Glu Glu Ser Val Tyr Asn Ser Gly Arg Lys Gly Pro Gly Pro Pro Ser Ser Asp Ala Ser Thr Ala Ala Pro
           CAG GCT CCT CCG CCT TCC TAC GAG GAA AGT GTT TAT AAT TCT GGT CGC AAA GGA CCC CCG CCA CCG TCG TCT GAT GCA TCC ACG GCG GCT CCG
           CAG GCT CCT CCG CCT TCC TAC GAG GAA AGT GTT TAT AAT TCT GGT CGC AAA GGA CCC CCG CCA CCG TCG TCT GAT GCA TCC ACG GCG GCT CCC
           Gln Ala Pro Pro Ser Tyr Glu Glu Ser Val Tyr Asn Ser Gly Arg Lys Gly Pro Gly Pro Pro Ser Ser Asp Ala Ser Thr Ala Ala Pro
      2425                                                      828                                858
           Pro Tyr Thr Asn Glu Gln Ala Tyr Gln Met Leu Leu Ala Leu Val Arg Leu Asp Ala Glu Gln Arg Ala Gln Gln Asn Gly Thr Asp Ser
           CCT TAC ACC AAC GAG CAG GCT TAC CAG ATG CTT CTC GCC CTC GTC CGT CTG GAC GCA GAG CAG CGA CGG CAG CAG AAC GGT ACA GAT TCT
           CCT TAC ACC AAC GAG CAG GCT TAC CAG ATG CTG CTG GCC CTG GCC CGT CTG GAC GCA GAG CAG CGA CGG CAG CAG AAC GGT ACA GAT TCT
           Pro Tyr Thr Asn Glu Gln Ala Tyr Gln Met Leu Leu Ala Leu Ala Arg Leu Asp Ala Glu Gln Arg Ala Gln Gln Asn Gly Thr Asp Ser
      2515                                                      878                                898
           Leu Asp Gly Gln Thr Gly Gln Asp Lys Gly Gln Lys Pro Asn Leu Leu Arg Arg Leu Arg His His Arg Lys Asn Gly Tyr Arg His Leu
           TTG GAC GGA CAG ACT GGC ACG CAG GAC AAG GGA CAG AAG CCC AAC CTG CTG CGA CGA CTG CGA CAC CAC CGG AAA AAC GGC TAC CGA CAC TTG
           TTG GAC GGA CAG ACT GGC ACG CAG GAC AAG GGA CAG AAG CCT AAC CTA CTA CGA CAT CGC CGG AAA AAC GGC TAC AGA CAC TTG
           Leu Asp Gly Gln Thr Gly Gln Asp Lys Gly Gln Lys Pro Asn Leu Leu Arg Arg Leu Arg His Arg Arg Lys Asn Gly Tyr Arg His Leu
      2605
```

FIG. 7F

```
                                                                907
       Lys Asp Ser Asp Glu Glu Glu Asn Val  OP
       AAA GAC TCC GAC GAA GAG GAA GAG AAC GTC TGAACCAAGAGGAGAAAAAAGTGACAGAGACTTGTGATATACGGGTAAACTGGACATCTAGGTGCT
2695   AAA GAC TCC GAC GAA GAG GAA GAG AAC GTC TGAACCAGGAGGAGAAAAAAAACTAGACAAAAAATATTGACACAGACTTGTGATATACGGGTAAACTGGATATCTAGGTGC
       Lys Asp Ser Asp Glu Glu Glu Asn Val  OP

GCATGTGTATTTGCTTTGTGATTTTCTTCGTAAGCTGTCTCAGCCTCTCACGGTCCGCTATGTTTTCAACCCGTATCTGAGCGGGGCGGGCGTCCGGTTGCCGGTGCCGCCG
2806   TGCATGTGTATTTTCTTTGTGATTTTCTTCGTAAGCTGTCACGGTCGCTATGTTTTCAACCCGTATCTGAGCGGGGCGGGCGTCCGGGTGCCGGTGGCCGGC

TCAGCGTTCGCAGCCCCGGCTCCGGCAGGGCTCGGGCAAGCGGCCAAGCGGCCTCATGTTCGAGATCGTGCCGGAGGCGCTCAGACGGGTTGATCAAGCATAA
2926   GTCAGCGTTCGCAGCCCCGGCTCCGGCAGGGCTCGGGCAAGCGGCCAAGCGGCCTCATGTCGAGATCGTGCCGAGGTGCAGACGGGTTGATCAAGCATA

GACGGGACGGTTGCCTCTCATGTTCTATCGAGAGATTAAACATTTGTTGAGTCATGACATGGTTGCCGTGCCGCGAGACCCTGTGTGGCCGTGCCGTATTCGTTT
3046   AGACGGGACGGCTGCCTCTCATGTTCTATCGAGAGATTAAACATTTGTTGAGTCATGACATGGTTGCCGTGCCGCGAGACCCTGTGTGGCCGTGCCGTATTCGTT

TCACACCTACGATCAAACGGACGCGTGCTCTTCTTCGACTCGCCCGAAAACGTGCCGCCGCCCTATCGTCGTTGCCTTCGGGGAACGTGTTGCGTTTCGGGCCACAGA
3166   TTCACACCTACGATCAGACGACGGACGCGTGCTCTTCTTCGACTCGCCCGAAAACGTGCCGCCGCCTATCGTCGTCGCCTTCGGGGAACGTGTTGCGTTTCTTCGGGCCCACAG

3286   ACACGGCTACAGTATCTGCGTC
       AACACGGCTACAGTATCTGCGT
```

FIG. 7G

ANTIBODY REACTIVITY WITH HCMV-gcI GLYCOPROTEINS/PEPTIDES

| gcI-mcAbs | | C'-DEPENDENT NEUTRALIZATION (Towne) | UNREDUCED gcI COMPLEXES (IP) | UNREDUCED gcI GLYCOPROTEINS | | | gcI CHYMOTRYPSIN FRAGMENTS | |
|---|---|---|---|---|---|---|---|---|
| | | | | gp130 (WB) | gp55 (WB) | gp93 (WB) | UNREDUCED (gp43/34) (WB) | REDUCED (gp34/30/28) (WB) |
| DOMAIN I | 41C2 | POSITIVE | POSITIVE | POSITIVE | POSITIVE | NEGATIVE | POSITIVE | POSITIVE |
| | 26B11 | NEGATIVE | POSITIVE | NEGATIVE | NEGATIVE | NEGATIVE | POSITIVE | NEGATIVE |
| | 39E11 | POSITIVE | POSITIVE | POSITIVE | POSITIVE | NEGATIVE | POSITIVE | POSITIVE |
| DOMAIN II | 9B7 | POSITIVE | POSITIVE | POSITIVE | POSITIVE | NEGATIVE | POSITIVE | POSITIVE |
| | 18F9 | POSITIVE | POSITIVE | POSITIVE | POSITIVE | NEGATIVE | POSITIVE | POSITIVE |
| | 34G7 | NEGATIVE | POSITIVE | NEGATIVE | NEGATIVE | NEGATIVE | POSITIVE | NEGATIVE |
| DOMAIN III | 11B4 | POSITIVE | POSITIVE | NEGATIVE | NEGATIVE | NEGATIVE | POSITIVE | POSITIVE |
| | 23B11 | POSITIVE | POSITIVE | POSITIVE | POSITIVE | NEGATIVE | POSITIVE | POSITIVE |
| HUMAN HCMV+ Sera | | POSITIVE | POSITIVE | POSITIVE | POSITIVE | NEGATIVE | POSITIVE | POSITIVE |

☐ POSITIVE   ▒ NEGATIVE

FIG. 8

ANTIBODY AND T CELL RECOGNITION SITES ON GLYCOPROTEINS COMPRISING THE GCI COMPLEX OF HUMAN CYTOMEGALOVIRUS

STATEMENT REGARDING FEDERALLY-FUNDED RESEARCH

This invention was made with government support under Department of Health and Human Services Grant No. HDMC 5 PO1GHD19937-03 GT. The government may have certain rights in the invention.

CROSS-REFERENCE TO RELATED APPLICATIONS

This application is a continuation-in-part of U.S. Pat. application Ser. No. 07/083,502, filed Aug. 7, 1987, which is in turn a continuation-in-part of U.S. Pat. application Ser. No. 06/933,789, filed Nov. 24, 1986, abandoned, and is also a continuation-in-part of U.S. Pat. application Ser. No. 07/214,302, filed July 1, 1988 (abandoned). The disclosures of all three applications are incorporated by reference herein.

FIELD OF THE INVENTION

The present invention is directed to a 93 kD glycopeptide of the gcI complex of human cytomegalovirus (HCMV) having unique B and T epitopes not present in other glycopeptides of gcI, to gcI glycopeptide fragments which represent the localization and minimization of continuous and discontinuous epitopes present in the major B cell antigenic region of the 55 kD glycopeptide of gcI, to recombinant expression vectors whose expression products are reactive with gcI-specific monoclonal antibodies and B and T lymphocytes, and to HCMV subunit vaccines and diagnostic methods.

BACKGROUND OF THE INVENTION

Human cytomegalovirus (HCMV) contains several families of antigenically related glycoprotein complexes, each comprised of two or more individual glycoproteins associated by disulfide bonds. These complexes and their constituent glycoproteins are present in the envelopes of HCMV virions, and are also expressed on the surface of HCMV-infected cells during permissive viral infection.

Convalescent sera from human subjects who have recovered from HCMV infection contain antibodies reactive with these envelope glycoproteins. Moreover, peripheral blood mononuclear cells (PBMCs) from seropositive subjects proliferate when stimulated with HCMV glycoproteins. Therefore, it is likely that these glycoproteins play an important role in protective immune responses, including antibody-mediated neutralization of extracellular virus, B and T cell responses to control or eradicate replicating intracellular virus to prevent cell-to-cell spread, and immune surveillance to prevent reactivation of latent HCMV infection.

Previously described HCMV envelope complexes and their constituent glycoproteins are summarized in Table I, below.

TABLE I

Human Cytomegalovirus Envelope Glycoproteins and Glycoprotein Complexes

| Complex(es) | MW(daltons) | Glycoproteins(s) | MW(daltons) | Genes(s) |
|---|---|---|---|---|
| gCI | 130,000–<br>180,000<br>>450,000 | gp130 (I)<br>gp 93 (I)<br>gp55 (I) | 130,000<br>93,000<br>55,000 | $U_L$<br>(.344–.360) |
| gCII93 | 93,000 | gp 90 (II93)<br>gp 52 (II93) | 90,000<br>50–52,000 | $U_S$<br>HXLFI-5<br>(.857–.879) |
| gCII200 | >200,000 | gp200 (II200)<br>gp 90 (II200)<br>gp 52 (II200) | >200,000<br>90,000<br>50–52,000 | |
| gCIII | 280,000 | gp145<br>gp 86 | 145,000<br>86,000 | $U_L$<br>(.450–.470) |
| Unassociated with any complex | | gp 93[1] | 93,000 | |
| | | Egp 48[2] | 48,000 | $U_L$-ORF3<br>(0.054–0.064) |

[1]This glycoprotein is distinct from gp93 of the gcI complex. See Kari et al., J. Virol., 60, 345-352, 1986. "Egp48"
[2]See the simultaneously filed U.S. Pat. application S.N. 07/328227 entitled "An Early Envelope Glycoprotein or Human Cytomegalovirus (HCMV); inventor Mark F. Stinski.

The family of antigenically related complexes with molecular weights of 130,000–180,000 and >200,000 daltons has been designated as gcI, which contains glycoproteins with molecular weights of 130,000 (gp130), 93,000 (gp93), and 55,000 (gp55). The glycoproteins were originally identified as gA by L. Pereira et.al., *Infection and Immunity*, 36; 924–932 (1982) (and in U.S. Pat. No. 4,689,225 to Pereira, Aug. 25, 1987) and subsequently designated as gB based on their extensive amino acid sequence homology with the gB glycoproteins of Herpes Simplex virus (HSV) and Epstein-Barr virus (EBV), and gp11 of Varicella zoster virus (VZV).

These gB glycoproteins derive from a single coding region in the unique long ($U_L$) region of the HCMV genome between map coordinates 0.344 and 0.360 as described by M. Mach et.al., *J. Gen. Virol.*, 67, 1461-1467 (1986). The gB gene may represent a primordial gene conserved among herpes viruses involved in biological functions critical to the evolution and survival of these viruses.

The gB gene was originally detected by expression of a cDNA library in λgt11 as detected with a monospecific rabbit antiserum reactive with the 55,000 dalton glycoprotein (gp55) of the gcI complexes. M. Cranage et. al., *EMBO J.*, 5, 3057-3063 (1986) subsequently expressed the gB gene in vaccinia and determined that gp55 was derived from a precursor with a molecular weight of 145,000. Cranage et.al. reported that the gB coding region predicts a polypeptide of 906 amino acids in the AD169 strain of HCMV.

Gretch et.al., *J. Gen. Virol.*, 69, 1205 (1988) subsequently reported that the synthesis of the gcI family of HCMV glycoproteins involves the glycosylation of a 95,000 dalton polypeptide encoded by the gB open reading frame to a stable simple N-linked glycoprotein intermediate of 138,000 daltons, gp138. Alternate proteolytic cleavage at several predicted dibasic protease recognition sites may account for the mature glycoproteins, gp55 and gp93, and possibly for gp130. Recent reports indicate that gp130 detected in detergent extracts of extracellular virions is a unique mature glycoprotein that is distinct from the glycosylated precursor, gp138. Taylor et.al., *Antiviral Research,* 10, 11-26, 1988.

Spaete et.al., *Virology,* 167, 207 (1988) reported the amino acid sequence of gB from Towne strain HCMV, which predicts a polypeptide of 907 amino acids with 95% homology to the gB gene in AD169. Analysis of the DNA sequence predicted an N-terminal signal sequence and a C-terminal transmembrane region composed of two domains of hydrophobic amino acids. Eucaryotic expression of the gB gene in COS cells (SV40-transformed simian cells) resulted in the synthesis of a gp130 precursor and a mature gp55 glycoprotein, as determined by reactivity with a neutralizing gcI-specific monoclonal antibody. N-terminal sequencing of purified gp55 showed that this glycoprotein is derived by proteolytic cleavage at dibasic amino acids 460-461 and represents the C-terminal region of gp130. Spaete et.al. further localized one neutralizing epitope to a 186 amino acid fragment of gp55 starting at the N-terminal amino acid 461 by expression of a truncated gB gene.

In sum, the gross characteristics of the gC I, II, and III complexes and corresponding glycoproteins have been partially determined. But, the antigenic regions of the complexes and glycoproteins have not as yet been mapped. Such studies would be useful in the development of vaccines and treatment of HCMV infections. Therefore, it is an object of the present invention to characterize biochemically and immunologically the antigenic regions of gp55 and gp93. In particular, another object is the characterization of the epitopes expressed on those proteins.

SUMMARY OF THE INVENTION

The present invention is directed to glycopeptides of the HCMV gcI complex which have unique B cell epitopes and T cell epitopes, glycopeptide fragments which represent epitopes in the major B cell antigenic region of gp55, recombinant expression vectors, vaccines, and diagnostic methods.

The B cell epitopal glycopeptide according to the invention is substantially pure, is immunogenic, has a molecular weight of about 93,000, and includes one or more unique B cell epitopes which are not present in the gp55 glycopeptide of gcI. Those "B cell epitopes" are epitopic sites, regions, antigenic determinants or regions within a polypeptide, glycopeptide or fragment thereof which do not react with or exhibit any substantial response to B lymphocytes, monoclonal antibodies produced by B lymphocytes, antibodies in HCMV seropositive human sera, or the like that are reactive with or respond to gp55. The "gp55" is the 55,000 dalton glycopeptide of the gcI complex of human cytomegalovirus.

The T cell epitopal glycopeptide according to the invention is substantially pure, is immunogenic, has a molecular weight of about 93,000, and includes one or more unique T cell epitopes which are not present in the gp55 glycopeptide of the gcI complex. These "unique T cell epitopes" are epitopic sites, regions, or antigenic determinants within a polypeptide, glycopeptide or fragment thereof which do not react with or exhibit any substantial response to T lymphocyte cell lines, T helper clones, peripheral blood mononuclear cells (PBMCs), or the like which are reactive with gp55.

The glycopeptide fragments of the antigenic region of gp55 according to the invention are enzymatic digestion products of gcI complex, are T cell org B cell immunogenic, have molecular weights of up to about 34 kD. Preferably the fragments include B cell epitopes composed of the amino acid sequences 560-565, 563-568, and 590-595 as well as amino acid sequence numbered herein as 560-569, these sequences being taken from the entire gcI amino acids sequence 1-907. Preferably the enzyme used in the fragment production is chymotrypsin.

The present invention is also directed to the provision of recombinant expression vectors. These vectors, which include the gB gene, are capable of expressing polypeptides that can be immunoprecipitated by gcI-specific monoclonal antibodies, or that stimulate proliferation of PBMCs or gcI-specific T cell lines or T helper clones. Recombinant expression vectors are also provided which are capable of expressing a fusion protein that reacts with gcI-specific T cell lines.

The present invention also is directed to a recombinant vaccinia virus expression vector capable of expressing a virus which stimulates the proliferation of gcI-specific T cell lines or T helper clones. Recombinant vaccinia virus expression vectors are also provided which induce a specific cytotoxic T cell response.

Advantageously, the identification, localization, and minimization of both unique and shared epitopes of the gp93 and gp55 glycopeptides of the gcI complex allows for the provision of subunit HCMV vaccines and diagnostic methods which utilize these epitopes.

A subunit HCMV vaccine would include, in combination with a pharmaceutically-acceptable carrier, an immunologically effective amount of a substantially pure glycoprotein of the gCI complex of human cytomegalovirus which has a molecular weight of about 93,000 and a B cell or T cell epitope not present in a 55,000 molecular weight effectively raise the titer of an antibody against HCMV in the blood of a mammal, or induce T helper cell ($T_h$) and cytotoxic T cell ($T_c$) response against HCMV when administered to a patient.

BRIEF DESCRIPTION OF THE DRAWINGS

FIG. 1B is a depiction of a model of a topographical antigenic map for HCMV glycoproteins in gcI complexes. Localization of B cell epitopes on HCMV are shown in FIG. 1A.

FIG. 2 is a schematic depiction of a molecular analysis of the antigenic domains of the gB (gcI) complex of HCMV.

Figure 6A:
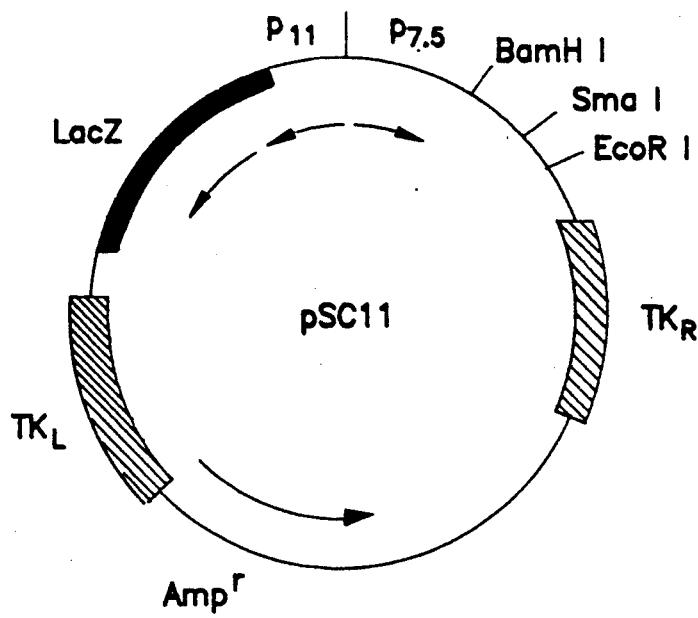

The top panel of FIG. 2 depicts the HCMV genome, which includes the unique long ($U_L$) coding region, extending from about 0.344 to about 0.360 map units.

The second panel of FIG. 2 depicts the base pair and amino acid numbering scheme for the gB (gcI) complex. The gcI glycoprotein designated herein as gp130, which extends from about amino acid 1 to about amino acid 907, is depicted next. Below gp130 is depicted the gcI glycoprotein designated herein as gp93, which has an approximate length of about 630 amino acids. Its N-terminus and the C-terminus positions are not known. The gcI glycoprotein designated herein as gp55 is depicted below gp93, and extends from about amino acid 461 to about amino acid 907. A 34,000 dalton chymotrypsin fragment of gcI, designated as Chym(R)-gp34 herein, is depicted below gp55, and originates with amino acid 482 at a Tyr-Ala chymotrypsin cleavage site and extends to about amino acid 782.

The last panel of FIG. 2 depicts the region of amino acids 461–671, which includes 3 B cell epitopes extending from amino acid 560–569. The three latter epitopes are amino acids 560–565 (18F9); 563–568(34G7); and 590–595(41C2) which are located by reactivity with monoclonal antibodies designated herein as 18F0, 34G7, and 41C2 respectively.

FIG. 3 is a schematic depiction of a plasmid map for pSP65 (produced by Boehringer Mannheim Biochemicals), a procaryotic expression vector into which the gB coding region was initially cloned for use in the detailed examples hereinbelow.

FIG. 4 is a schematic depiction of a plasmid map for pRIT5 (produced by Pharmacia), a procaryotic expression vector containing a protein A fusion vector having multiple cloning sites, as further described in the detailed examples hereinbelow.

FIG. 5 is a schematic depiction of the nucleotide locations of 11 overlapping pRIT5 fusion proteins selectively cloned from the pRIT5 expression vector, designated pRIT5 -1 through pRIT5 -11, respectively, which were utilized as described in the detailed examples hereinbelow.

Figure 6B:
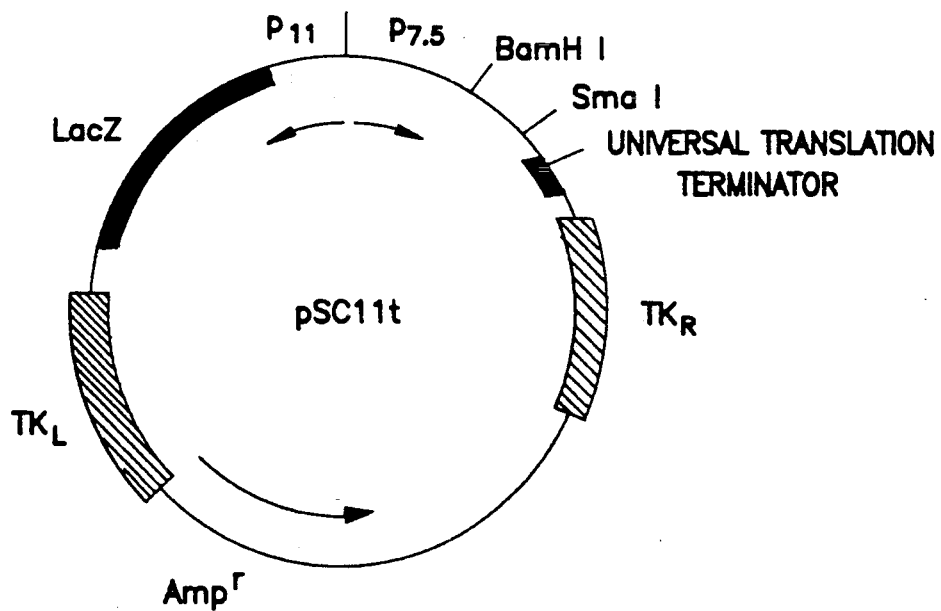

FIGS. 6A and 6B, is a schematic depiction of a plasmid map for pSC11 and pSC11t, respectively, (a gift from B. Moss, NIAID), a eucaryotic vaccinia virus vector into which the gB coding region was cloned as described in the detailed examples hereinbelow.

Figure 7B:
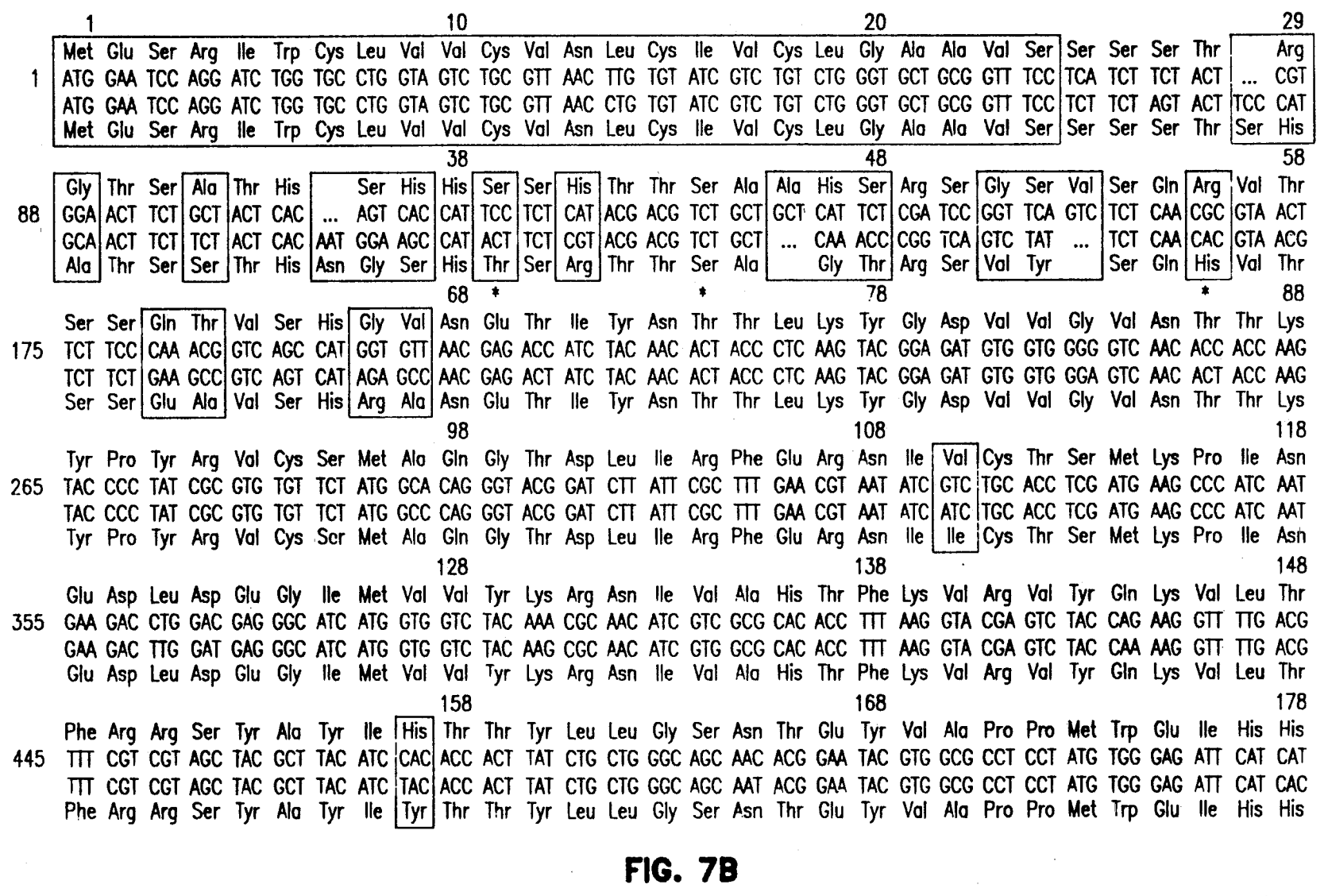
Figure 7C:
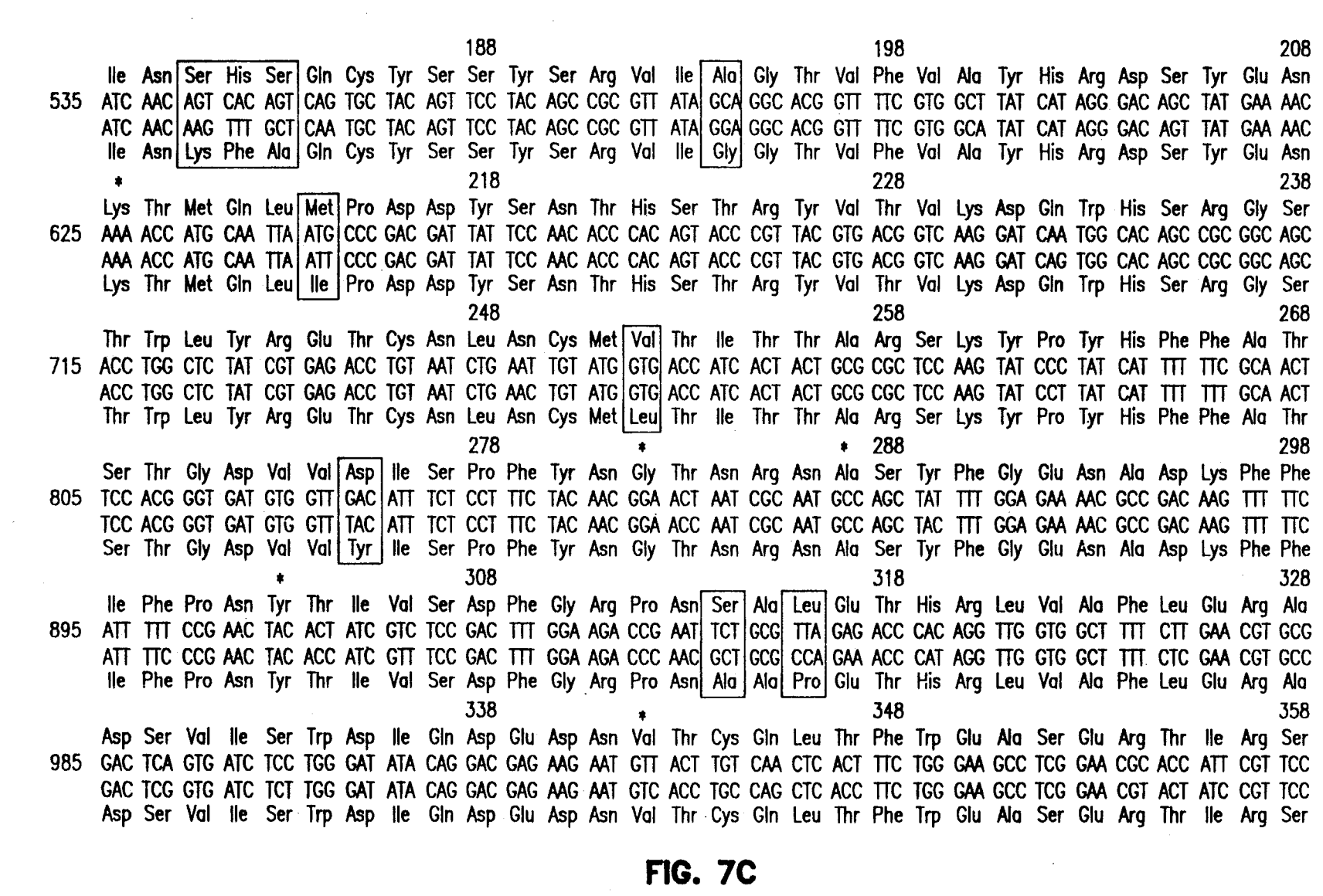
Figure 7D:
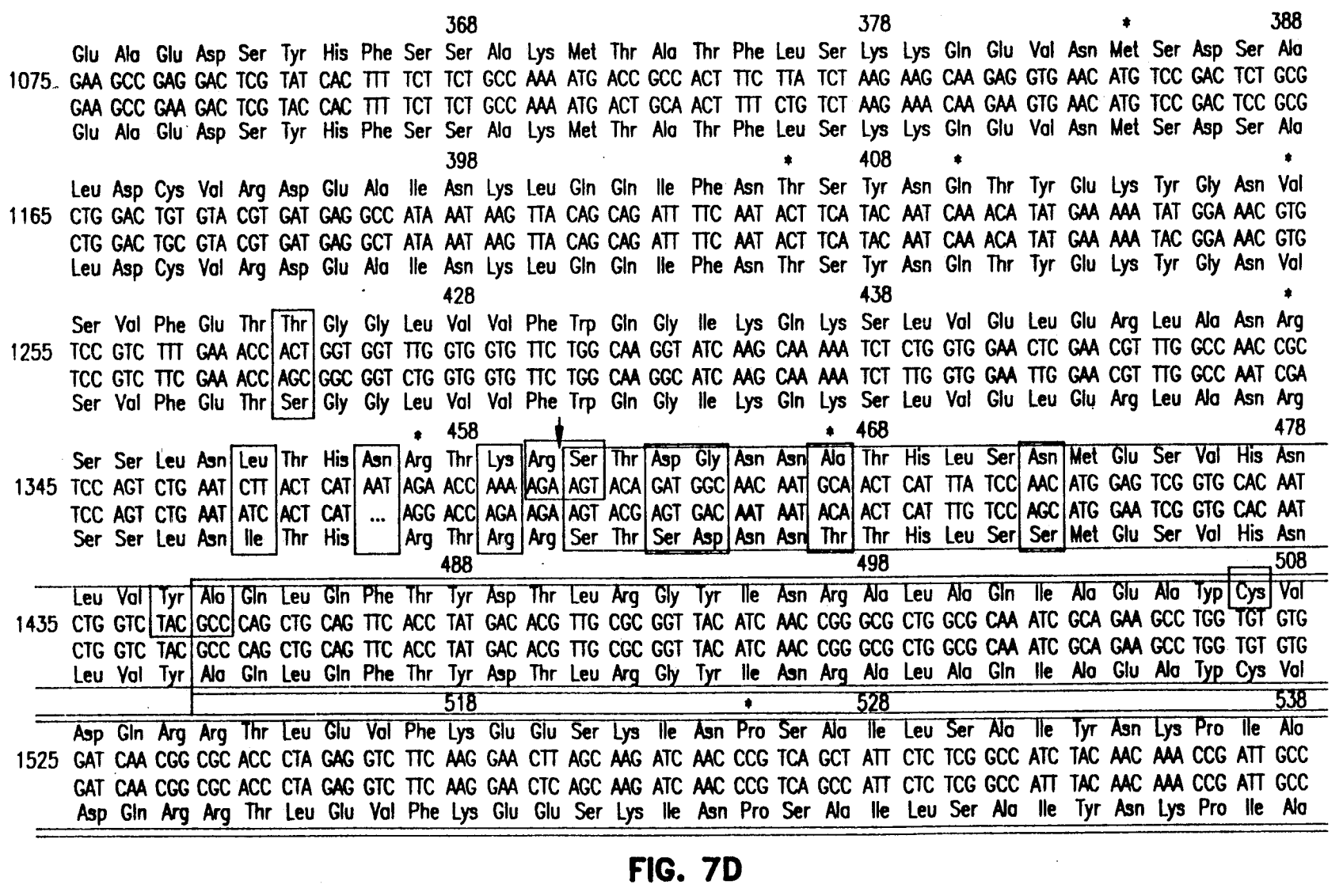
Figure 7E:
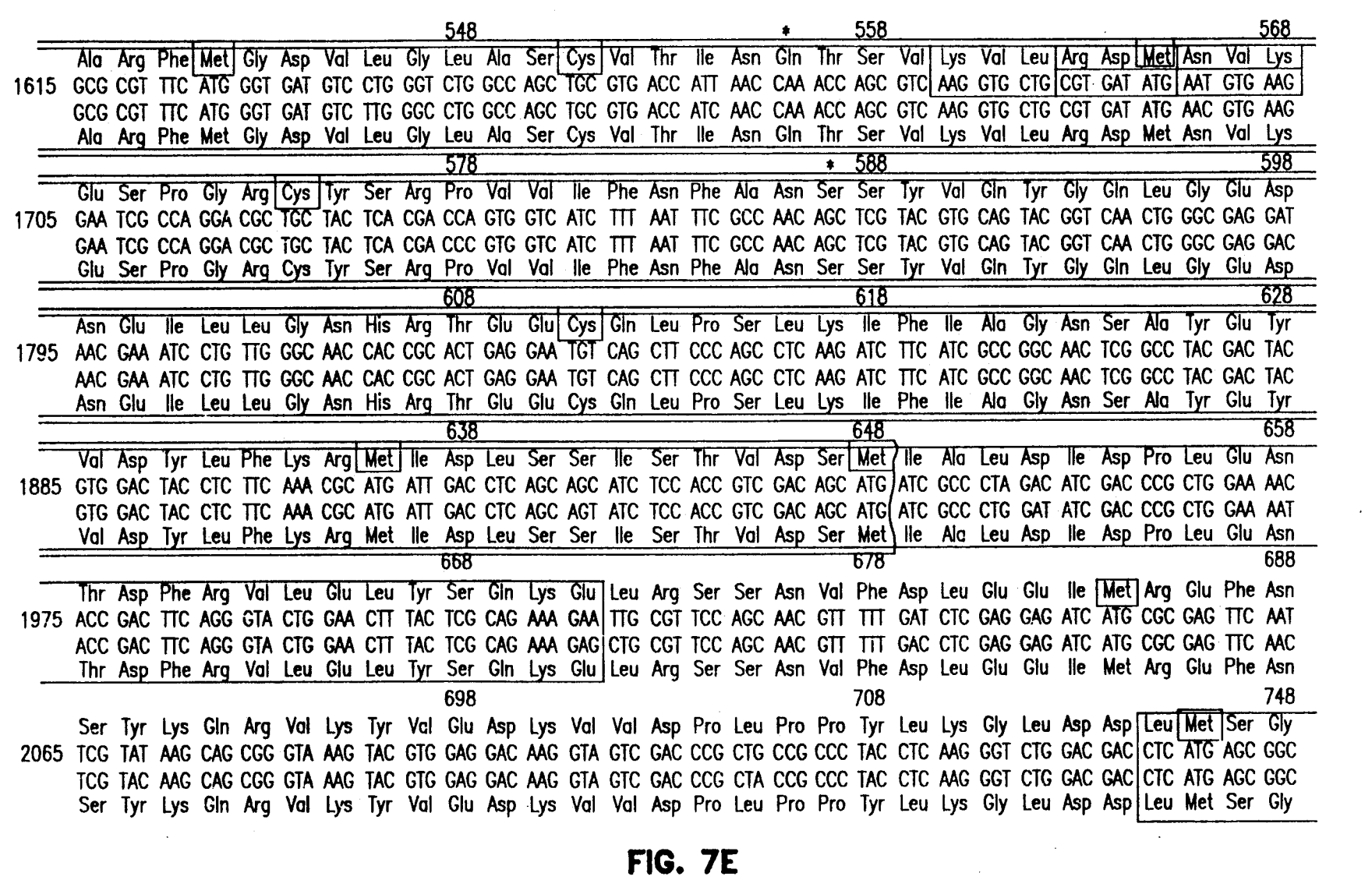

FIGS. 7A–7G illustrate the amino acid sequence of the gcI complex and the codon sequence of the gB gene (spaete et.al., *Virology*, 167, 207, 1988).

FIG. 8 is a table indicating antibody reactivity with HCMV-gcI glycoproteins/peptides.

DETAILED DESCRIPTION OF THE INVENTION

In co-pending U.S. Pat. application Ser. Nos. 933,789, (abandoned) and 83,502, filed Nov. 24, 1986 and Aug. 7 1987, respectively, the disclosures of which are incorporated by reference herein, substantially pure immunogenic 93 kD and 55 kD glycopeptides on the membrane envelope of HCMV and their derivation from gp138, a precursor glycoprotein, were disclosed. These glycopeptides are associated with other envelope glycopeptides by means of disulfide bonds. The 93 kD glycopeptide immunoreacts in Western Blot with CMV-seropositive human sera but does not react in Western Blotwith monoclonal antibodies that immunoprecipitate gp55 of the gcI complexes. This indicates that certain human antibodies recognize unique B cell epitopes on gp93.

The present invention is based in part upon the discovery that gp93 contains unique amino acid sequences expressing antigenic determinants recognized by B and T lymphocytes which are different from the antigenic determinants expressed on gp55. The glycopeptides disclosed in the foregoing section constitute the results, in part, of this discovery. As used herein, the term "substantially-pure" is intended to mean that the glycopeptide complexes or the glycopeptides have been extracted from their natural association on the membrane envelope of HCMV with other membrane components and from internal nuclear or capsid components of HCMV.

In co-pending U.S. Pat. application Ser. No. 07/214,302, (abandoned) filed July 1, 1988, the disclosure of which is incorporated herein by reference, antibody and T cell responses to unreduced and reduced gcI glycopeptide fragments obtained by proteolytic digestion of native complexes with chymotrypsin or trypsin were characterized. The results of this study are depicted in Table II, below.

TABLE II

HCMV gcI (Glyco)peptide Complexes and Individual (Glyco)peptides Obtained by Proteolytic Digestion of HCMV gcI and Detected by HCMV-Specific McAbs and/or HCMV−(+) Human Sera[1]

| | Unreduced gcI Glycopeptide Complexes: | | Reduced gcI Glycopeptide Complexes: | |
|---|---|---|---|---|
| | Treatment of gcI Complexes | | | |
| | Glycosylated | Non-Glycosylated | Glycosylated | Non-Glycosylated |
| Undigested | >200,000[2] | 35,000 | 130,000 | |
| | 130,000–190,000 | 20,000 | 93,000 | 12,000 |
| | | | 53,000 | |
| Chymotrypsin Fragments | 43,000 | | | |
| | 34,000–43,000 | 20,000 | 34,000 | Several |
| Trypsin Fragments | 106,000 | 34,000 | 47,000–52,000 | |
| | 44,000 | 20,000 | 47,000 35,000 | Several |

[1]Detection method was immoprecipitation and/or Western Blot
[2]Molecular weights expressed in daltons In those applications, it was indicated that the eight epitopes of the major B cell antigenic region of gp55 are contained within these proteolytic fragments. Human convalescent sera from seropositive individuals also react with these fragments.

Using polyclonal and monoclonal gcI-specific T cell lines, it has now been found according to the present invention that gcI complexes contain T cell epitopes expressed within and outside of the gp55 region. Therefore, the present invention is directed to further localization of T cell epitopes of gcI glycoproteins. More specifically, the present invention contemplates glycopeptides with epitopes which are unique to amino acid sequences in the N-terminal region of the gB polypeptide that are contained within gp93 but not within gp55.

In co- application U.S. Pat. application No. 83,502, filed Aug. 7, 1987, the disclosure of which is incorporated by reference herein, there is disclosed the generation of several murine B-cell hybridomas producing monoclonal antibodies (McAbs) specifically reactive with gcI complexes containing three glycoproteins gp130, gp93, and gp55. The individual gcI-specific McAbs were shown to inhibit or augment the simultaneous binding of other of the gcI-specific MCAbs in a manner which suggested at least 7 distinct antigenic sites in 3 separate domains of gcI. It was concluded that these three domains were the major B cell antigenic region of gp55.

The present invention is based in part upon the elucidation of these domains. It has been discovered that these domains contain at least eight epitopal sites which are B cell reactive. In particular, three of these eight epitopes have now been particularly identified and sequenced as the glycopeptide fragments representing localized, minimal antigenic structures of gp55. These three immunoreact with monoclonal antibodies 18F9, 34G7 and 41C2 as mentioned above. The fragments compose the continuous and discontinuous epitopes in the major B cell antigenic region of gp55.

The invention will be further described by reference to the following detailed examples, wherein the methodologies are as described below. The disclosures of the cited references are incorporated by reference herein.

METHODS

Immunoprecipitation. For immunoprecipitation, Protein A-Sepharose Cl-4B beads (Sigma-Aldrich, St. Louis, Miss.) were prepared by incubation with goat anti-mouse IgG (H and L) and washed with phosphate-buffered saline (PBS) before use. Whole extract or glycopeptides and glycopeptide complexes obtained by ion-exchange HPLC were incubated with monoclonal antibody (preparation, infra) in PBS containing 0.1% NP-40 for 1.5 hours with constant mixing. In some cases, 0.1% sodium dodecylsulfate (SDS) was used in place of NP-40. The prepared Protein A-Sepharose CL-4B beads were then added to the antigen-antibody solution and allowed to react for an additional 1.5 hours with constant mixing. The beads were washed three times with PBS containing 0.1% NP-40. Following the final wash, proteins associated with the beads were solubilized for SDS-PAGE.

Preparation of Monomer. Isolated HCMV disulfide-linked glycopeptide complexes were reduced by addition of dithiothreitol to a final concentration of 10 mM (DTT, U.S. Biochemicals, Cleveland, OH) in the presence of 8M Urea. The reaction was allowed to proceed at room temperature for 2-24 hours with constant stirring. Alkylation of the reduced sulfhydryl group was done by adding 5-10 mg iodoacetamide and allowing the reaction to proceed at room temperature for an additional hour.

Gel Filtration HPLC of Individual HCMV Glycopeptides. Samples containing 1% SDS were subjected to gel filtration HPLC using a Varian system. Gel filtration was performed coupling TSK 3000 SW and 4000 SW gel filtration columns (Toyo Soda, Tokyo, Japan) in series and eluting isocratically with 50 mM sodium phosphate, pH 7.0, containing 0.1% SDS. The flow rate was 0.3 ml/minute. Absorbance was monitored at 275 nm and fractions collected were also monitored for radio-activity.

SDS-Polyacrylamide Gel Electrophoresis and Fluorography. SDS-PAGE was done with 5-15% polyacrylamide slab gel gradients following the method of Laemmli. Samples were solubilized by boiling for three minutes in the presence of 4% SDS. After the samples were cooled to room temperature, urea and beta-mercaptoethanol (BME) were added so that samples contained 5% BME and 2M urea. Tritium was detected by fluorography using Enlighting (DuPont/NEN, Boston, Mass.).

Preparation of Viruses. HCMV Towne strain and AD169 strain were grown with or without 3H-glucosamine on human skin fibroblast cultures, harvested and purified on sucrose gradients as described previously (Kari et.al., *J. Virol.*, 60, 345-352 (1986)). The purified virus was resuspended in Tris-NaCl buffer (50 mM Tris hydrochloride, 150 mM NaCl pH 7.4), and extracted with 1% Nonidet P-40 (NP-40, Sigma Chem. Co., St. Louis, MO) in Tris-NaCl buffer (50 mM Tris hydrochloride, 10 mM NaCl buffer (50 mM hydrochloride, 10 mM NaCl., 2 mM phenylmethyl sulfonylfluoride pH 7.5) as described by Kari et.al., in *J. Virol.*, 60, 345-352 (1986). Uninfected skin fibroblasts were extracted in a similar fashion for use as negative controls. Reduction and alkylation of HCMV Towne NP-40 crude extracted material was performed as described by Kari et.al., *J. Virol*, 60, 345-352 (1986). All detergent extracted viral or control fibroblast materials were passed over an Extracti-Gel D column and eluted with water to remove the detergent.

*Generation of Murine Monoclonal Antibodies to HCMV.* The production of mouse hybridomas secreting mcAbs to HCMV proteins was performed as previously described (Kari et. al., *J. Virol.*, 60, 345-352 (1986)). The antibodies produced involved three separate fusion experiments using either AD169 or Towne strain purified HCMV virions. Balb/C mice were immunized for 2, 5 or 10 months. Spleen cells from immunized mice were fused with Sp2-2-Ag14 myeloma cells (American Tissue Culture Collection) using polyethylene glycol as the fusing agent.

Resulting hybrid cells were screened for specific antibody production to HCMV using an enzyme-linked immunosorbent assay (ELISA). Antigens used in the ELISA assay were either purified HCMV Towne Strain or AD169 strain whole virions or HCMV Towne NP-40 extracted material or NP-40 extracted material from uninfected skin fibroblasts. Ascites fluids from expanded clones were purified for IgG using high performance hydroxyapatite chromatography (HPLC) (Juarez-Salinas et.al., *Biotechniques, 2, 164* (1984)).

The titer of fractions collected from the column was measured with respect to HCMV-specific activity using the ELISA assay. The protein content of the fractions was determined using the BioRad protein assay (BioRad) and purified mouse IgG as a standard. Only fractions with the highest titers from each run were used for subsequent experiments.

*Immunoprecipitation.* Monoclonal antibodies were allowed to immunoprecipitate $^3$H-glucosamine-labelled HCMV Towne NP-40 extracted proteins which were unreduced or reduced and alkylated prior to immunoprecipitation. Proteins were solubilized in sodium dodecyl sulfate (SDS) and separated by SDS polyacrylamide gel electrophoresis. The tritium-labelled glycoprotein bands in the gel were identified by fluorography as described (Kari et.al., J. Virol., 60, 345-352 (1986)).

*Western Blot.* For Western Blot assays, purified HCMV Towne strain whole virus was solubilized with SDS and separated by 5-15% gradient polyacrylamide gel electrophoresis.

The proteins on the gel were subsequently electroblotted onto nitrocellulose paper with a BioRad transblot apparatus. The paper was blocked with 3% gelatin in Tris buffered saline (TBS, 20 mM Tris, 500 mM NaCl pH 7.5). The mcAbs in ascites fluid were diluted 1/500 in 1% gelatin in TBS, and allowed to bind to the paper overnight at room temperature. The paper was washed with PBS-0.05% Tween 20 (polysorbate 20), and alkaline phosphatase-labelled goat anti-mouse IgG (KPL) diluted 1/2000 with 1% gelatin in TBS was added and allowed to incubate for one hour at room temperature. The paper was washed once again and the substrate 5-bromo-4-chloro-3-indolyl-phosphate/nitroblue tetrazolium in 0.1 M Tris buffer solution (KPL) was added. Reaction of the antigen-antibody complex with the substrate resulted in the formation of an insoluble purple product. The reaction was stopped by immersing the paper in water.

ELISA Assay for Detection of Glycoprotein in Tissue Culture Supernatants. Microtiter wells in 96-well microtiter plates are pre-coated with a first HCMV glycoprotein-specific monoclonal antibody as the capture antibody. Included in each plate are a blank well, a well for an uninfected fibroblast control and a glycoprotein positive control and an glycoprotein positive control well in addition to wells for patient samples After coating with the capture antibody, the microtiter wells are washed once with buffer (PBS-0.5% Tween). Sample solutions are solubilized in PBS-1% Np-40 in each tissue culture well, and are then dispensed into individual microtiter wells. Blank, negative skin fibroblast and glycoprotein positive control samples are included with each clinical sample determination.

Five µl of biotinylated, glycoprotein-specific monoclonal antibody which recognizes a different epitope on gcI than that recognized by the first monoclonal antibody, are then added to each microtiter well as a detection antibody. The microtiter plate is then placed in a plastic bag and incubated at 37° C. for 1 hour. Wells are then washed 4 times with wash buffer (PBS-0.05% Tween), 100 µl of streptavidin-peroxidase is added and the plate is incubated for 30 minutes at 37° C. in a plastic bag. Wells are then washed 4 times with wash buffer and then one time with distilled water. Orthophenylenediamine (OPD) substrate (100 µl) is added and reacted for 15 minutes at room temperature. The reaction is then stopped with 25 µl of 5 N $H_2SO_4$. After 10 minutes, the microtiter plate is read with a Dynatech plate reader at 490 nm or by visual colorometric reading. This method has been shown to detect glycoprotein at a total protein concentration of 10 nanograms.

EXAMPLE 1

Initial Characterization of B and T Cell Responses to HPLC-Purified gcI and Proteolytic Cleavage Fragments A. B Cell Recognition As described in detail in U.S. Pat. application Ser. No. 83,502, the disclosure of which is incorporated herein by reference, murine gcI-specific monoclonal antibodies recognize multiple epitopes in three domains clustered in a single major antigenic region containing: (a) continuous neutralizing and non-neutralizing epitopes; and (b) conformation-dependent epitope(s) eliciting monoclonal antibodies which block neutralization by other monoclonal antibodies.

Antibody Reactivity with HCMV-gcI Glycoproteins/Peptides

A simultaneous competitive ELISA assay was used to identify eight gcI-specific monoclonal antibodies (mcAbs) reactive with unique continuous or conformation-dependent epitopes in three domains comprising a major B cell antigenic region of gcI (Lussenhop et.al., Virology, 160, 308, 1988). FIG. 8 summarizes the results. Individual mcAbs in domains I and II either augment or inhibit the binding of other gcI-specific mcAbs, and exhibit similar effects on virus neutralization in a plaque reduction assay. McAbs reactive with conformation-dependent epitope(s) in domain III inhibit binding and neutralizing activity of all other gcI-specific mcAbs.

All of the gcI-specific mcAbs antibodies recognizing continuous epitopes immunoprecipitate gcI complexes and react with gp130, gp55, and proteolytic cleavage fragments obtained by digestion with chymotrypsin in Western blot analysis. However, these same mcAbs are either non-reactive or minimally reactive with gp93. gcI-specific mcAbs recognizing conformational epitopes react with unreduced gcI complexes and chymotrypsin fragments, but not with reduced gcI glycoproteins or proteolytic fragments. Human HCMV-positive convalescent sera also recognize B cell epitope(s) on gcI complexes and proteolytic fragments. All react with gp130 and gp55 in Western blot. In addition, some but not all sera react with gp93.

All of the gcI-specific monoclonal antibodies listed in FIG. 8 immunoprecipitated gcI complexes and unreduced proteolytic cleavage fragments, and reacted with gp130 and gp55 in Western Blot analysis. However, these same monoclonal antibodies were either non-reactive or minimally reactive with gp93 in Western Blot, suggesting that gp93 may not share the major antibody recognition site with gp55.

The results summarized in FIG. 8 indicate that human HCMV-positive convalescent sera immunoprecipitated gcI complexes as well as proteolytic fragments containing the major B cell antigenic domain. All sera reacted with gp130 and gp55 in Western Blot analysis; however, some but not all sera reacted with gp93. This result suggests that unique determinants on gp93 are involved in the human antibody response which are not recognized by any of the murine gcI-specific monoclonal antibodies described thus far.

B. T Cell Responses to HCMV-gcI Glycoproteins peripheral blood mononuclear cells (PBMCs) from all HCMV-seropositive adults proliferate when stimulated with whole HCMV virions, whereas only two-thirds respond to HPLC-purified gcI (Liu et.al., J. Virol., 62, 1066, 1988). gcI-responsive PBMCs also responded to gp130, gp55, and gp93 obtained by electrocution from polyacrylamide gels. HCMV-specific T helper ($T_h$) clones reactive with gcI as well as clones reactive with other structural (glyco)proteins are detected in gcI responders (data not shown), suggesting that (glyco)-proteins other than gcI are important in cell-mediated immunity.

TABLE III

| | T Cell Responses to HCMV-gcI Glycoproteins | | |
|---|---|---|---|
| | HCMV-Specific T Cell Lines/Clones | | |
| | KM-3UR (Polyclonal gcI-specific T cell line) | WRCT3#3 (gcI-specific $T_h$ clone) | WRCL26 (Non-gcI specific $T_h$ clone) |
| Medium control | 3,808 | 142 | 61 |
| HCMV virions[a] | 36,610 | 12.835 | 3,785 |
| gcI[b] | 20,128 | 13,997 | 74 |
| gp55[c] | 10,643 | 6,590 | 108 |
| gp93[c] | 18,293 | 11,438 | 106 |
| gp130[c] | 13,340 | 11,299 | 82 |

TABLE III-continued

| T Cell Responses to HCMV-gcI Glycoproteins | | |
|---|---|---|
| HCMV-Specific T Cell Lines/Clones | | |
| KM-3UR (Polyclonal gcI-specific T cell line) | WRCT3#3 (gcI-specific T_h clone) | WRCL26 (Non-gcI specific T_h clone) |
| BSA 2,337 | 118 | 57 |
| Acrylamide 2,382 | 56 | 63 |

[a] virions purified by sucrose gradient ultracentrifugation of extracellular virus from supernatants of HCMV-infected fibroblasts
[b] unreduced gcI complexes separated from detergent extracts of HCMV virions by anion exchange HPLC and immunoprecipitated with gcI-specific mcAb 41C2
[c] individual gcI glycoproteins separated from reduced gcI complexes in SDS-PAGE and isolated by electroelution.

T Cell Responses to Proteolytic Fragments of HCMV-gcI

The experiments summarized at Table IV show that gcI-specific polyclonal T cell lines proliferate when stimulated with trypsin or chymotrypsin gcI fragments as well as whole gcI complexes. However, certain gcI-specific $T_h$ clones react with gcI complexes and trypsin fragments but not with chymotrypsin fragments. These data suggest that T cell epitope(s) are expressed on gp55 in the region spanning amino acids 482-782 defined by chym(R)-gp34. In addition, T cell epitope(s) are expressed in the C-terminal region of the gB polypeptide sequence contained in gp93 but not gp55. These data suggest that there is a major B cell antigenic region expressed on gp130 and gp55 recognized by the gcI-specific mcAbs, and in addition, unique determinants on gp93 involved in the human antibody response.

TABLE IV

| T Cell Responses to Proteolytic Fragments of HCMV-gcI | | |
|---|---|---|
| HCMV-Specific T Cell Lines/Clones | | |
| | SJK (Polyclonal HCMV-specific T cell line) | WRCT3#3 (gcI-specific T_h clone) |
| Medium control | 81 | 256 |
| HCMV virions[a] | 46,055 | 20,497 |
| gcI[b] | 5,954 | 11,509 |
| trypsin fragments[c] | 22,961 | 34,420 |
| chymotrypsin fragments[c] | 11,119 | 377 |

[a] virions purified by sucrose gradient ultracentrifugation of extracellular virus from supernatants of HCMV-infected fibroblasts
[b] unreduced gcI complexes separated from detergent extracts of HCMV virions by anion exchange HPLC and immunoprecipitated with gcI-specific mcAb 41C2
[c] unreduced trypsin and chymotrypsin fragments obtained by proteoltic digestion of unreduced gcI complexes purified as above ([b])

EXAMPLE 2

Molecular Analysis of B and T Cell Epitopes on gcI

A. Location of Glycopeptide Fragments on the gB Sequence by N-terminal Sequencing An abundant reduced chymotrypsin gcI glycopeptide fragment of molecular weight 34,000 was purified by gel filtration. N-terminal sequencing on a Porton gas phased sequenator located this fragment to the N-terminal half of gp55, starting with amino acid 482 at a Tyr-Ala chymotrypsin cleavage site. The chym(R)-gp34 fragment is depicted in FIG. 2. Deglycosylation of chym(R)-gp34 with N-glyconase resulted in a non-glycosylated polypeptide having a molecular weight of about 30,000 daltons. Assuming the average molecular weight of an amino acid is 100, chym(R)-gp34 extends to about amino acid 782 in the predicted transmembrane region of gp55, and includes substantially all of the extracellular domain of gp55.

All monoclonal antibodies as well as seropositive convalescent sera reacted with the 34 kD reduced chymotrypsin fragment as shown in Table IV.

B. Definitive Epitope Analysis to Characterize the Major B Cell Antigenic Domain(s) of gp55

Hexapeptides overlapping by a single amino acid for the region of gcI spanning amino acids 461-671 were generated using the pin-synthesis method originally described by Geysen et.al., (Proc. Natl. Sci., 81, 3998 (1984)) (see FIG. 3). The multi-pin-synthesis technology, manufactured by Cambridge Research Biochemicals under license from Commonwealth Serum Laboratories, was designed to synthesize nanomole amounts of overlapping peptides from known sequences using f-moc chemistry. Reactivity of the gcI-specific monoclonal antibodies with peptides irreversibly bound to the pins was then determined by ELISA according to a procedure provided by the manufacturer.

A B cell epitope was located by reactivity of gcI-specific (Domain II) monoclonal antibody 34G7 to amino acids 563-568, shown in the last panel of FIGS. 1 and 2. Amino acid 565 within this region is a methionine, which upon cleavage with cyanogen bromide (CNBr) eliminated binding of 34G7 to this epitope.

A second B cell epitope, which overlaps the 34G7 epitope, was located by reactivity of gcI-specific (domain II) mcAb 18F9 to amino acids 560-565 as shown in FIGS. 1A, 1B, and 2.

A third B cell epitope has been located by reactivity of gcI-specific (domain I) mcAb 41C2 to amino acids 590-595 as shown in FIGS. 1A, 1B and 2.

The proximity of these epitopes to amino acids associated with loop structures (Proline) and intra-chain disulfide bonds (Cysteine) are consistent with the proposed topographical model depicted in FIG. 1A.

The results of the hexapeptide synthesis confirmed that antibody responses to gp55 involve primarily a series of continuous and spacially related epitopes comprising a single major antigenic domain. Thus, a polypeptide derived by proteolytic cleavage of biochemically purified gcI, the molecular expression product of the portion of the HCMV genome coding for this antigenic region, or relevant synthesized peptides in this region can be useful in vaccines to induce neutralizing antibody responses in humans against HCMV, and can also be useful as antigen to detect the presence of antibodies reactive with gp55/gcI in human or animal sera.

EXAMPLE 3

Expression of gB in Procaryotic and Eucaryotic Expression Vectors for T Cell Epitope Analysis A. Procaryotic Expression in pSP65

The gB coding region derived from Towne strain HCMV, located at about 0.344 to about 0.360 map units in the HCMV genome, was initially cloned into the procaryotic expression vector pSP65 under the control of an inducible promoter. This promoter facilitates the high level production of mRNA transcripts from the foreign gene of interest in bacteria. FIG. 3 depicts the plasmid map for pSP65.

The resulting gB-mRNA was then translated in vitro in rabbit reticulocyte lysates. The p95 polypeptide product of gB was identified by $^{35}$S-met/SDS-PAGE. The gB polypeptide was immunoprecipitated by gcI-specific monoclonal antibodies and stimulated proliferation of PBMCs and gcI-specific $T_h$ clones in proliferation assays. The preparation of these gcI-specific Th clones is described in detail in co-pending U.S. Pat. application Ser. No. 07/024,571, (abandoned) filed Mar. 11, 1987, the disclosure of which is incorporated by reference herein. Table V, below, depicts the level of $^3$H-thymidine incorporation by the $T_h$ clones with whole HCMV virions, HPLC-purified gcI, and various translation lysates of the mRNA of gcI.

restriction enzymes designated as pRIT5 -1 through pRIT5 -11, respectively. Three fusion proteins derived by expression of the pRIT5 -2, pRIT5 -4, and pRIT5 -9 recombinants were used to locate the immunodominant T cell epitopes of gB. The pRIT5 -2 fusion protein designated herein as ProteinA-gcI-2 (base pairs 938-2136) comprised the N-terminal end of gB outside of gp55, while the pRIT5 -4 fusion protein designated herein as ProteinA-gcI-4 (b.p. 1983-2730) comprised a

TABLE V

Comparison of Reactivity of T Helper Cell Clones to HPLC-purified gcI and Protein Translated from gcI mRNA

| Antigen: | $^3$H-thymidine incorporation in counts per minute with $T_h$ Clones: | | | |
|---|---|---|---|---|
|  | SP-CN/T3-3 | SP-CN/T5-10 | SP-CN/T5-43 | SP-CN/T3-4 |
| Control | 311 | 275 | 210 | 122 |
| Whole HCMV virions | 33,003 | 27,079 | 77,933 | 26,498 |
| HPLC purified gcI | 19,670 | 2,822 | 273 | 169 |
| Translation lysate with no mRNA | 110 | ND | 107 | ND |
| Translation lysate with gcI mRNA | 4,394 | 1,784 | 427 | 131 |
| Translation lysate with nucleocapsid of black beetle mosaic virus mRNA | 234 | 118 | 143 | ND |
| Translation lysate with mRNA transcribed from a region upstream of gcI | 181 | 347 | 190 | 242 |

As indicated by the data of Table V, the HCMV-$T_h$ clones SP-CN/T3—3 and SP-CN/T5-10 which responded to HPLC-purified gcI also responded to a polypeptide translated from gcI mRNA in a rabbit reticulocyte lysate system. The HCMV-$T_h$ clones SP-CN/T5-43 and SP-CN/T3-4 which did not respond to HPLC-purified gcI did not respond to polypeptide translated from gcI mRNA, either. Furthermore, SP-CN/T3—3 and SP-CN/T5-10 did not respond to lysate control nor translated products of other mRNA. Therefore, it was concluded that continuous T cell epitope(s) are expressed on the gB polypeptide backbone.

B. Procaryotic Expression in pRIT5

The gB coding region (0.344-0.360 m.u.) was then cloned into the procaryotic expression vector, pRIT5 (Pharmacia, Piscataway, NJ). FIG. 4 depicts the construction of pRIT5. The pRIT5 cloning vector is comprised of a promoter, the open reading frame for staphylococcal protein A, and a multiple cloning site downstream of the staphylococcal protein A ORF which can be used to introduce foreign genes in frame with protein A. The high level expression of hybrid protein and convenient single-step purification using an IgC Sepharose 6FF affinity gel column (Pharmacia) allowed for the isolation of significant quantities of fusion proteins for T cell epitope mapping.

Unique restriction sites were identified in the gB coding region to allow for the selective cloning of 11 overlapping gB fragments representing the entire open reading frame of the gB (gcI) gene. FIG. 5 depicts the nucleotide locations of these fragments, and the unique region including both unique gp93 sequences as well as the N-terminal region of gp55 including much of the major B cell antigenic region. The pRIT5 -9 fusion protein designated herein as ProteinA-gcI-9 (b.p. 2786-3791) comprised the C-terminal region of gp55. Based on the reactivity of a gcI-specific polyclonal T cell line, designated herein as KM, with ProteinA-gcI-2 and ProteinA-gcI-4, but not with ProteinA-gcI-9, the T cell epitopes were located in the N-terminal two-thirds of the gB polypeptide. KM T cell line is a polyclonal T cell line which was produced by repeated stimulation of peripheral blood mononuclear cells obtained from an HCMV-seropositive donor (KM) with HPLC-purified gcI complexes. This polyclonal T cell line is comprised of HCMV-specific T cells reactive with all T cell epitopes expressed on gcI complexes and its constituent glycoproteins. It is, therefore, useful for screening of peptide fragments of larger gcI glycoprotein structures for epitope analysis.

Table VI, below, depicts the proliferation of the KM gcI-specific T cell line in the presence of the various fusion proteins. The level of $^3$H-thymidine incorporation was assayed following elimination with various antigens, including the fusion proteins expressed by the pRIT5 -2, pRIT5 -4, and pRIT5 -5 recombinants.

TABLE VI

Lymphocyte Proliferation Assay with Protein A Fusion Proteins (KM gcI-Specific T Cell Line)

| Antigen | $^3$H-Thymidine Incorporation counts per minute Positive | $^3$H-Thymidine Incorporation Negative |
|---|---|---|
| Control |  | 304 ± 156 |
| CMV | 11,731 ± 5,673 |  |
| Vaccinia-gcI | 1,244 ± 420 |  |
| Protein A |  | 329 ± 95 |
| ProteinA-gcI-2 | 2,132 ± 527 |  |
| ProteinA-gcI-4 | 1,990 ± 435 |  |
| ProteinA-gcI-9 |  | 639 ± 322 |

The data of Table VI suggest that gcI contains T cell epitope(s) in the N-terminal region, perhaps overlapping with the gcI major B cell antigenic domain. More specifically, the data suggest that the gcI-specific T cell response includes $T_h$ reactive with epitopes shared among gp130, gp55, and gp93, presumably in the same region as that containing the major B cell antigenic region of gp55, as well as $T_h$ reactive with unique epitopes expressed only on gp93.

In addition, the peptide sequence in pRIT5 -2 outside of gp55 (i.e., on gp93) also contains T cell epitope(s), indicating that this region of the polypeptide may be important in cell-mediated immunity. This can be seen from a comparison of FIGS. 2 and 5. Recombinant pRIT5 -2 ending at bp2136 does not contain the sequence within gp55 which begins about bp2300. Therefore, the T cell response to pRIT5 -2 locates one or more T cell epitopes to a region of the gB sequence outside of gp55, but which is included in gp93.

EXAMPLE 4

Eucaryotic Expression of gB in Vaccinia

The gB (gcI) coding region was cloned into the eucaryotic vaccinia virus vector pSC11 (provided by B. Moss, National Institute of Allergy and Infectious Diseases, Bethesda, MD) at the SmaI site. FIG. 6, panel A, depicts the construction of the pSCII vector. Panel B of FIG. 6 depicts a modification of pSC11, designated pSC11t, in which there has been inserted a universal translation terminator to facilitate transcription and translation of full-length mRNA from foreign genes cloned in frame into this vector. The gene was introduced into vaccinia virus by homologous recombination between the TK gene of the wild strain vaccinia virus and the TK flanking sequences on either side of gB which had previously been inserted into the pSC11 plasmid. The resulting recombinant vaccinia virus was identified by expression of the $\beta$ galactosidase gene using Xgal from Bethesda Research Laboratories Life Technologies, Inc. (Gaitersburg, MD), and was purified by three cycles of plaque purification.

The vaccinia-gB recombinant, designated as VAC-gB herein, allows for eucaryotic expression in mammalian cells to allow for post-translational processing such as glycosylation which may be critical for conformation-dependent immune recognition. Expression of gB in fibroblasts infected with the VAC-gB recombinant was confirmed by indirect immunofluorescence using a gcI-specific monoclonal antibody. Furthermore, the gcI-specific mcAb 41C2 immunoprecipitated all three gcI glycoproteins, gp130, gp93 and gp55, in lysates of vaccinia-gB infected fibroblasts. A polyclonal gcI-specific T cell line (KM) and several gcI-specific $T_h$ clones (KM-A, KM-B, KM-C, KM-G, KM-H, KM-J, KM-3, AND WRCT3#3) were then stimulated with whole HCMV virions and lysates of fibroblasts infected either with wild strain vaccinia or with VAC-gB. Table VII, below, depicts the results of a lymphocyte proliferation assay for the T cell line and $T_h$ clones, which were labelled with $^3$H-thymidine, and added to whole HCMV virions and to lysates of wild strain vaccinia-infected or VAC-gB-infected fibroblasts.

TABLE VII

Lymphocyte Proliferation Assay with $^3$H-Thymidine-Labelled T Cells in Whole Virions and Wild Strain Vaccinia versus Vaccinia-gcI Recombinant

| T Cells | Medium Control | HCMV[1] | Vaccinia[2] | Vaccinia-gcI[3] |
|---|---|---|---|---|
| | gcI-Specific T Cell Line: | | | |
| KM | 304 ± 156 counts per minute | 11,731 ± 5,673 | ND | 1,244 ± 420 |
| | HCMV-Specific $T_h$ Clones: | | | |
| KM-A | 60 ± 7 | 15,778 ± 1,360 | 74 ± 12 | 647 ± 83 |
| KM-B | 59 ± 7 | 1,894 ± 587 | 57 ± 6 | 465 ± 37 |
| KM-C | 74 ± 14 | 17,071 ± 1,638 | 89 ± 11 | 4,565 ± 834 |
| KM-G | 195 ± 63 | 3,161 ± 519 | 117 ± 26 | 714 ± 204 |
| KM-H | 72 ± 23 | 2,007 ± 245 | 77 ± 7 | 67 ± 23 |
| KM-J | 90 ± 15 | 6,252 ± 636 | 55 ± 5 | 2,619 ± 246 |
| KM-3 | 95 ± 18 | 2,530 ± 688 | 55 ± 2 | 1,058 ± 300 |
| WRCT3#3 | 46 ± 10 | 8,839 ± 1,351 | ND | 5,337 ± 970 |

[1]Whole HCMV virions
[2]Lysate of fibroblasts infected with wild strain vaccinia
[3]Lysate of fibroblasts infected with vaccinia-gB recombinant As shown in Table VII, all the T cell line/clones responded to whole HCMV, and all but one $T_h$ clone (KM-H) also reacted specifically to gcI expressed in vaccinia (VAC-gB-infected fibroblasts).

HCMV-specific polyclonal T cell lines stimulated by cell-associated HCMV were then tested for cytotoxic activity against autologous fibroblasts infected with HCMV, vaccinia pSC11 which did not contain a foreign gene, or vaccinia-HCMV gB recombinants as shown in Table VIII below.

TABLE VIII

Cytotoxic Activity of Polyclonal T Cell Structures Stimulated by Cell-Associated HCMV

| % Specific Lysis Measured by $^{51}$Cr Release[1] | | HCMV-Infected Fibroblasts | pSC11 Vaccinia | Vaccinia-gB gene Recombinant |
|---|---|---|---|---|
| Effector Cells | E:T[2] | — | | |
| WRC anti-HCMV T Cell Line | 50:1 | 0.4 ± 1.5 | 40.0 ± 6.7 | 19.4 ± 13.8 | 36.7 ± 5.1 |
| | 25:1 | −1.7 ± 0.5 | 33.7 ± 2.7 | 25.3 ± 3.0 | 25.5 ± 1.5 |
| | 12:1 | −1.7 ± 0.8 | 24.0 ± 3.1 | 23.3 ± 2.0 | 23.1 ± 4.0 |
| SKJ anti-HCMV T Cell Line | 16:1 | 4.0 ± 0.8 | ND | 3.8 ± 4.0 | 36.4 ± 51.0 |
| | 8:1 | −4.0 ± 0.9 | ND | 6.4 ± 1.4 | −1.4 ± 2.0 |

[1]Autologous uninfected or HCMV/vaccinia-infected fibroblasts used as target cells
[2]Ratio of effector cells to target cells (v/v) in sample.

Products of vaccinia-HCMVgB were shown to induce specific cytotoxic activity, suggesting that gcI proteins are targets for the cytotoxic T cell response.

In summary, linear and/or conformational epitopes expressed on the polypeptide encoded by gB, as well as unique and/or shared epitopes expressed on gp55 and gp93, are involved in recognition by antibodies and $T_h$ and $T_c$ cells. Thus, it is likely that gp93, as well as gp55, is an appropriate candidate for a subunit HCMV vaccine.

The invention has been described with reference to various specific and preferred embodiments and techniques. However, it should be understood that many variations may be made while remaining within the spirit and scope of the invention.

What is claimed is:

1. A substantially pure glycopeptide having the following properties:
   (a) has a molecular weight of about 93,000 daltons as determined by SDS-PAGE technique under reducing conditions,
   (b) is a subunit member of the gCI complex of human cytomegalovirus,
   (c) contains a B cell or T cell epitode which is not present in another gCI complex subunit glycopeptide having a molecular weight of about 55,000 daltons as determined by SDS-PAGE technique under reducing conditions,
   (d) associated by at least one disulfide bond with other gCI complex subunit glycopeptides having molecular weights of about 130,000 daltons and about 55,000 dalton as determined by SDS-PAGE under reducing conditions,
   (e) associated with said gCI complex subunit glycopeptides in the gCI complex under non-reducing conditions.

2. A glycopeptide according to claim 1 wherein the epitope is a T cell epitope.

3. A glycopeptide according to claim 1 wherein the epitope is a B cell epitode.

4. The glycopeptide of claim 3 which does not react with a monoclonal antibody selected from the group consisting of 41C2, 26B11, 39E11 9B7, 18F9, 34G7, 11B4, and 23B11, and said monoclonal antibody does react with the said about 55,000 dalton glycoprotein.

5. The glycopeptide of claim 1 wherein said glycopeptide reacts with human cytomegalovirus seropositive convalescent sera.

6. A vaccine against human cytomegalovirus comprising an immunologically effective amount of the glycopeptide of claim 1 in combination with a pharmaceutically acceptable carrier.

7. A method for raising the titer of an antibody against human cytomegalovirus in the blood of a mammal, comprising the step of administering to the mammal a vaccine of claim 6.

8. A method for inducing T helper cell ($T_h$) and T cytotoxic cell response against human cytomegalovirus comprising administering to the patient a vaccine of

* * * * *

UNITED STATES PATENT AND TRADEMARK OFFICE
CERTIFICATE OF CORRECTION

PATENT NO. : 5,124,440

DATED : June 23, 1992

INVENTOR(S) : Richard C. Gehrz et al.

It is certified that error appears in the above-identified patent and that said Letters Patent is hereby corrected as shown below:

Item [75] Title page, inventor, should read --Bruce E. Kari--.

At column 1, line 10, for "GHD" read --HD--

At column 2, line 56, for "Δgt11" read --λgt11--.

At column 4, line 42, after "weight" insert --glycoprotein of the gCI complex. The vaccine would--.

At column 5, line 10, for "18FO" read --18F9--.

At column 6, line 4, for "Blotwith" read --Blot with--

At column 6, line 40, for "53,000" read --55,000--

At column 9, line 23, after "samples" insert --.--

At column 9, line 38, for "streptayidin" read "streptavidin"

At column 10, line 43, after "Glycoproteins" insert --The experiments summarized at Table III show that--

At column 10, line 50, for "electrocution" read --electroelution--

At column 11, line 36, for "Fraqments" read --Fragments--

At column 11, line 49, for "proteoltic" read --proteolytic--

At column 13, line 2, for "TH" read --$T_h$--

UNITED STATES PATENT AND TRADEMARK OFFICE
CERTIFICATE OF CORRECTION

PATENT NO. : 5,124,440

DATED : June 23, 1992

INVENTOR(S) : Richard C. Gehrz et al.

It is certified that error appears in the above-identified patent and that said Letters Patent is hereby corrected as shown below:

At column 15, line 22, for "Small" read --SmaI--

At column 18, line 29, after "of" insert --claim 6--

Signed and Sealed this

Twenty-sixth Day of April, 1994

Attest:

BRUCE LEHMAN

Attesting Officer  Commissioner of Patents and Trademarks